United States Patent [19]
Thompson et al.

[11] Patent Number: 6,100,448
[45] Date of Patent: *Aug. 8, 2000

[54] INCREASING EXPRESSION OF TRANSGENES IN PLANT CELLS USING INSULATOR ELEMENTS

[75] Inventors: William Thompson; George Allen; Scots Mankin, all of Raleigh, N.C.

[73] Assignee: North Carolina State University, Raleigh, N.C.

[ * ] Notice: This patent is subject to a terminal disclaimer.

[21] Appl. No.: 09/227,633

[22] Filed: Jan. 8, 1999

Related U.S. Application Data

[63] Continuation of application No. 08/692,847, Aug. 1, 1996, Pat. No. 6,037,525.

[51] Int. Cl.⁷ .......................... C12N 15/00; C12N 15/29; C12N 15/82; A01H 3/00
[52] U.S. Cl. ..................... 800/278; 800/295; 800/298; 435/468; 435/419; 435/320.1; 536/23.6; 536/24.1; 536/23.7
[58] Field of Search ..................... 800/295, 298, 800/278; 435/468, 419, 320.1; 536/23.6, 24.1, 23.7

[56] References Cited

PUBLICATIONS

Kellum et al. Cell. vol. 64, pp. 941–950, Mar. 8, 1991.
V. G. Corces, "Keeping enhancers under control", *Nature*, 376 462–463 (1995).
Cal, et al., "Modulation of enhancer–promoter Interactions by insulators in the Drosophila embryo", *Nature* 376 533–536 (1995).
Allen, et al., "High–Level Transgene Expression in Plant Cells: Effects of a Strong Scafold Attachment Region from Tobacco" *The Plant Cell* 8 899–913 (1996).
Allen, et al., "Scaffold Attachment Regions Increase Reporter Gene Expression in Stably Transformed Plant Cells" *The Plant Cell* 5 603–613 (1993).
Kellum et al., "A position–effect assay for boundaries of higher order chromosomal domains" *Cell* 64:941–950 (Mar. 1991).
Mlynarova et al., "Reduced position effect in mature transgenic plants conferred by the chicken lysozyme matrix–associated region" *The Plant Cell* 6:417–426 (Mar. 1994).
Farkas et al., "Sequence of scs and scs' Drosophila DNA fragments with boundary function in the control of gene expression" *Nucleic Acids Research* 20:2604 (1992).

*Primary Examiner*—Gary Benzion
*Assistant Examiner*—Thomas Haas
*Attorney, Agent, or Firm*—Myers Bigel Sibley & Sajovec

[57] ABSTRACT

A method of making recombinant plant cells having reduced variability of expression of foreign genes therein is described herein. The method comprises (a) providing a plant cell capable of regeneration; and (b) transforming the plant cell with a DNA construct comprising an expression cassette, which construct comprises a transcription initiation region, a structural gene positioned downstream from the transcription initiation region and operatively associated therewith, and an insulator (or "boundary element") positioned (i) 5' to the transcription initiation region, (ii) 3' to the structural gene, or (iii) both 5' to the transcription initiation region and 3' to the structural gene. DNA constructs useful for carrying out the method and plant cells and plants produced by the method are also disclosed.

41 Claims, 1 Drawing Sheet

INCREASING EXPRESSION OF TRANSGENES IN PLANT CELLS USING INSULATOR ELEMENTS

This application is a cont. of Ser. No. 08/692,847 filed Aug. 1, 1996, now U.S. Pat. No. 6,037,525.

FIELD OF THE INVENTION

The present invention relates to methods for reducing the variability of expression of foreign genes in plant cells, along with DNA constructs containing insulator or boundary elements for carrying out such methods, and the plant cells and plants so produced.

BACKGROUND OF THE INVENTION

Agricultural biotechnology, and particularly plant biotechnology, has become recognized as one of the principal areas for the application of biotechnology techniques. Systems exist for transforming plant cells and regenerating complete plants from the transformed cells; structural gene and gene regulatory regions continue to be identified; and the need for plants with genetically engineered traits such as insect resistance and drought resistance remains strong.

A problem with the expression of foreign genes in plants is the clonal variation in the expression of the same gene in independent transformants: a problem referred to as "position effect" variation. No completely satisfactory method of obviating this problem has yet been developed, and there is accordingly a continued need for solutions to this problem.

SUMMARY OF THE INVENTION

In view of the foregoing, a first aspect of the present invention is a method of making recombinant plant cells having reduced variability of expression of foreign genes therein. The method comprises (a) providing a plant cell capable of regeneration; and (b) transforming the plant cell with a DNA construct comprising an expression cassette, which construct comprises, in the 5' to 3' direction, a transcription initiation region, a structural gene positioned downstream from the transcription initiation region and operatively associated therewith, and an insulator (or "boundary element") positioned (i) 5' to the transcription initiation region, (ii) 3' to the structural gene, or (iii) both 5' to the transcription initiation region and 3' to the structural gene. One or more scaffold attachment regions (or "SARs") may optionally be included in the construct in addition to the insulator region(s). The transforming step is preferably followed by regenerating shoots, roots, or both shoots and roots (i.e., an intact plant) from the transformed cells. Preferably the DNA construct comprises, in the 5' to 3' direction, a first insulator, a transcription initiation region, a structural gene positioned downstream from the transcription initiation region and operatively associated therewith, a termination region, and a second insulator.

A second aspect of the present invention is a DNA construct comprising an expression cassette, which construct comprises, in the 5' to 3' direction, a transcription initiation region, a structural gene positioned downstream from the transcription initiation region and operatively associated therewith, and an insulator positioned: (i) 5' to the transcription initiation region, (ii) 3' to the structural gene, or (iii) both 5' to the transcription initiation region and 3' to the structural gene.

A third aspect of the present invention is a DNA construct as given above carried by a plant transformation vector.

A fourth aspect of the present invention is a plant cell containing a DNA construct as given above.

A fifth aspect of the present invention is a recombinant plant comprising transformed plant cells, the transformed plant cells containing a heterologous DNA construct comprising an expression cassette, which construct comprises, in the 5' to 3' direction, a transcription initiation region, a structural gene positioned downstream from the transcription initiation region and operatively associated therewith, and an insulator positioned: (i) 5' to the transcription initiation region, (ii) 3' to the structural gene, or (iii) both 5' to the transcription initiation region and 3' to the structural gene.

While scaffold attachment regions, or SARs, have previously been indicated as useful for reducing expression variability and increasing gene expression in plants (see, e.g., G. Allen et al., *The Plant Cell* 5, 603–613 (1993); G. Allen et al., *The Plant Cell* 8, 899–913 (1996)), SARs and insulators are structurally and functionally distinct, and insofar as applicants are aware no such activity has been suggested or described for insulators in plant cells.

The foregoing and other objects and aspects of this invention are explained in detail in the drawings herein and the specification set forth below.

BRIEF DESCRIPTION OF THE DRAWINGS

FIG. 1A shows cells transformed with a control 35SP::luc::nosT expression cassette construct.

FIG. 1B shows cells transformed with a control RB7MAR::35SP:luc:nosT::RB7MAR expression cassette construct.

FIG. 1C shows cells transformed with an insulator-containing scs::35SP::luc::nosT::scs' construct.

DETAILED DESCRIPTION OF THE INVENTION

Figure 1:
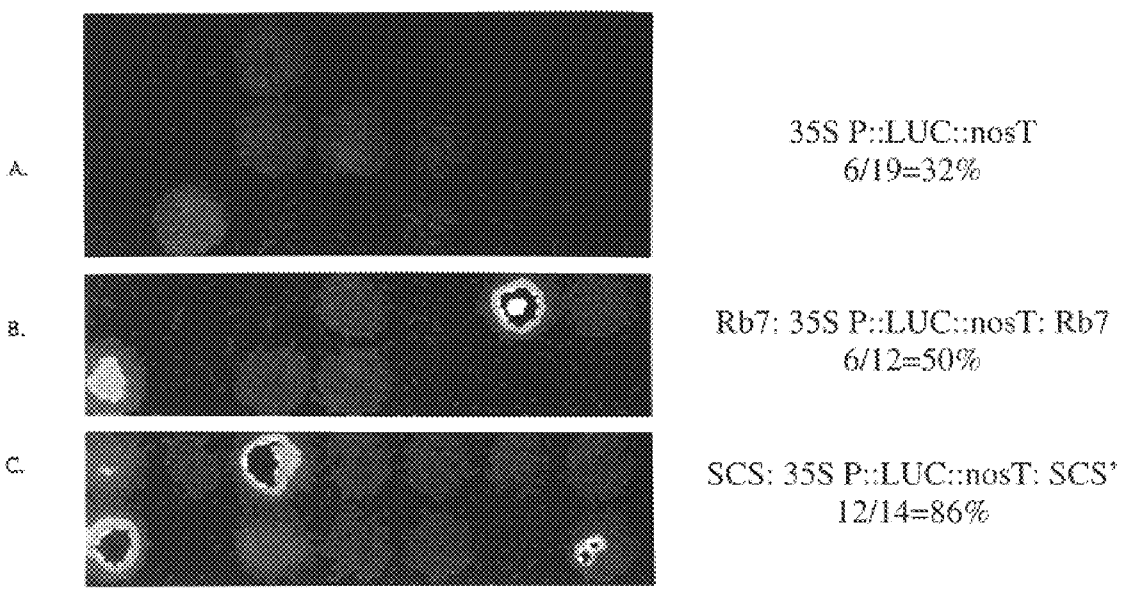
FIG. 1 shows the effect of an insulator on luciferase expression in transgenic bombarded NT1 cells. A luciferase reporter gene and unlinked kanamycin resistance gene were introduced into NT1 cells by co-transformation with a mixture containing a luciferase reporter plasmid and a separate plasmid carrying a nos::nptII selectable marker gene. The mixture of DNAs (in a 4:1 molar ratio) was introduced into tobacco NT1 cells via microprojectile bombardment. Equimolar amounts of each different luciferase construct were used. After establishing stably transformed cell lines, expression was assayed by adding luciferin to packed cells in a black 96-well ELISA plate, incubating overnight, and imaging in a Hamamatsu photon counting system for 30 minutes.

Nucleotide sequences are presented herein by single strand only, in the 5' to 3' direction, from left to right.

The present invention may be carried out with cells from a variety of different plants. As used herein, the term "plant" or "plants" means vascular plants, including both monocots and dicots, and both angiosperms and gymnosperms.

The term "operatively associated," as used herein, refers to DNA sequences on a single DNA molecule which are associated so that the function of one is affected by the other. Thus, a transcription initiation region is operatively associated with a structural gene when it is capable of affecting the expression of that structural gene (i.e., the structural gene is under the transcriptional control of the transcription initiation region). The transcription initiation region is said to be "upstream" from the structural gene, which is in turn said to be "downstream" from the transcription initiation region.

The term "insulator" (or "chromatin insulator", "boundary element") has its conventional meaning in the art, and refers to a DNA segment that prevents enhances located on one side of the insulator or boundary element from acting on promoters located in the adjacent domain. V. Corces, *Nature* 376, 462 (Aug. 10, 1995). Insulators useful in carrying out the present invention may be of any origin, including both plant and animal species, but are generally of eukaryotic origin. Plant insulators may be taken from any suitable plant, including those plants specified below; animal insulators may be taken from any suitable animal including insects (e.g., Drosophila), mammals (e.g., rat, mouse, dog, cat), birds (e.g., chicken, turkey), etc.; and insulators may be taken from other eukaryotes such as fungi (e.g., *Saccharomyces cereviceae*). Where two insulators are employed, they may be the same or different. The insulator may be a fragment of a naturally occurring insulator, so long as it retains function as an insulator. The length of the insulator is not critical, but may generally be from 100, 200, or 300 bases up 2000 or 3000 bases in length. The scs insulators (this term including downstream scs' insulators) are currently preferred.

To test a candidate insulator for activity as an insulator, one may simply clone the candidate insulator into a construct comprising, 5' to 3', a constitutive enhancer, the candidate insulator, an inducible promoter (e.g., an HSP70 promoter), and a reporter gene (e.g., gus, luciferase). Plant cells are then transformed with the construct by any suitable means as described herein, and (optionally) plants created from the cells. Expression of the reporter gene should be constitutively suppressed, but activated by the appropriate signal (e.g., temperature) to the inducible promoter. See, e.g., R. Kellum et al., *Molec. Cell. Biology*, 2424–2431 (May 1992).

DNA constructs, or "expression cassettes," of the present invention preferably include, 5' to 3' in the direction of transcription, a transcription initiation region, a structural gene positioned downstream from the transcription initiation region and operatively associated therewith, an insulator positioned: (i) 5' to the transcription initiation region, (ii) 3' to the structural gene, or (iii) both 5' to the transcription initiation region and 3' to the structural gene, and, optionally, a termination sequence including stop signal for RNA polymerase and a polyadenylation signal for polyadenylase (e.g., the nos terminator). The promoter should be capable of operating in the cells to be transformed. The termination region may be derived from the same gene as the promoter region, or may be derived from a different gene.

As noted above, the expression cassette of the invention may include a scaffold attachment region (or "SAR") which may be nested within or positioned outside of any insulator. Thus, the SAR or SARs may be positioned: (i) 5' to the transcription initiation region (e.g., at a position either 5' or 3' to any insulator that is positioned 5' to the transcription initiation region), (ii) 3' to the structural gene (e.g., at a position either 5' or 3' to any insulator that is positioned 3' to the structural gene), or (iii) both 5' to the transcription initiation region and 3' to the structural gene (e.g., with the 5' SAR at a position either 5' or 3' to any insulator that is positioned 5' to the transcription initiation region, and with the 3' SAR positioned either 5' or 3' to any insulator that is positioned 3' to the structural gene). Preferably, the insulator or insulators are positioned outside of the SAR or SARs (that is, the SAR is positioned between the insulator and the structural gene).

SARs (also called matrix attachment regions, or "MARs") that are used to carry out the present invention may be of any suitable origin. In general, the SAR of any eukaryotic organism (including plants, animals, and yeast) may be employed, as SARs are highly conserved among the eukaryotes. See, e.g., G. Allen et al., *The Plant Cell* 5, 603–613 (1993); M. Eva Luderus et al., *Cell* 70, 949–959 (1992); G. Hall et al., *Proc. Natl. Acad. Sci. USA* 88, 9320–9324 (1991). For example, animal SARs are shown to be operational in plants in P. Breyne, *The Plant Cell* 4, 463–471 (1992), and yeast SARs are shown to be operational in plants hereinbelow. Plant SARs may be taken from any suitable plant, including those plants specified above and below; animal SARs may be taken from any suitable animal including mammals (e.g., dog, cat), birds (e.g., chicken, turkey), etc.; and SARs may be taken from other eukaryotes such as fungi (e.g., *Saccharomyces cereviceae*). Where two scaffold attachment regions are employed, they may be the same or different. The length of the SAR is not critical so long as it retains operability as an SAR, with lengths of from 400 to 1000 base pairs being typical.

The transcription initiation region, which includes the RNA polymerase binding site (promoter), may be native to the host plant to be transformed or may be derived from an alternative source, where the region is functional in the host plant. Other sources include the Agrobacterium T-DNA genes, such as the transcriptional initiation regions for the biosynthesis of nopaline, octapine, mannopine, or other opine transcriptional initiation regions; transcriptional initiation regions from plants, such as the ubiquitin promoter; root specific promoters (see, e.g., U.S. Pat. No. 5,459,252 to Conkling et al.; WO 91/13992 to Advanced Technologies); transcriptional initiation regions from viruses (including host specific viruses), or partially or wholly synthetic transcription initiation regions. Transcriptional initiation and termination regions are well known (see, e.g., dGreve, *J. Mol. Appl. Genet.* 1, 499–511 (1983); Salomon et al., *EMBO J.* 3, 141–146 (1984); Garfinkel et al., *Cell* 27, 143–153 (1983); Barker et al., *Plant Mol. Biol.* 2, 235–350 (1983)); including various promoters isolated from plants (see, e.g., U.S. Pat. No. 4,962,028) and viruses (such as the cauliflower mosaic virus promoter, CaMV 35S).

The transcriptional initiation regions may, in addition to the RNA polymerase binding site, include regions which regulate transcription, where the regulation involves, for example, chemical or physical repression or induction (e.g., regulation based on metabolites, light, or other physicochemical factors; see, e.g., WO 93/06710 disclosing a nematode responsive promoter) or regulation based on cell differentiation (such as associated with leaves, roots, seed, or the like in plants; see, e.g., U.S. Pat. No. 5,459,252 disclosing a root-specific promoter). Thus, the transcriptional initiation region, or the regulatory portion of such region, is obtained from an appropriate gene which is so regulated. For example, the 1,5-ribulose biphosphate carboxylase gene is light-induced and may be used for transcriptional initiation. Other genes are known which are induced by stress, temperature, wounding, pathogen effects, etc.

The term "structural gene" herein refers to those portions of genes which comprise a DNA segment coding for a protein, polypeptide, or portion thereof, possibly including a ribosome binding site and/or a translational start codon, but lacking a transcription initiation region. The term can also refer to copies of a structural gene naturally found within a cell but artificially introduced. The structural gene may encode a protein not normally found in the plant cell in which the gene is introduced or in combination with the transcription initiation region to which it is operationally associated, in which case it is termed a heterologous structural gene. Genes which may be operationally associated with a transcription initiation region of the present invention for expression in a plant species may be derived from a chromosomal gene, cDNA, a synthetic gene, or combinations thereof. Any structural gene may be employed. The structural gene may encode an enzyme to introduce a desired trait into the plant, such as glyphosphate resistance; the structural gene may encode a protein such as a *Bacillus thuringiensis* protein (or fragment thereof) to impart insect resistance to the plant; the structural gene may encode a plant virus protein or fragment thereof to impart virus resistance to the plant. The term "structural gene" as used herein is also intended to encompass a DNA encoding an antisense agent that will bind to a particular mRNA in the plant cell and downregulate translation thereof. See, e.g., U.S. Pat. No. 5,107,065 to Shewmaker et al.

Expression cassettes useful in methods of the present invention may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly a plant host. The markers may be protection against a biocide, such as antibiotics, toxins, heavy metals, or the like; provide complementation, for example by imparting prototrophy to an auxotrophic host; or provide a visible phenotype through the production of a novel compound. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are β-glucuronidase, providing indigo production; luciferase, providing visible light production; NPTII, providing kanamycin resistance or G418 resistance; HPT, providing hygromycin resistance; and the mutated aroA gene, providing glyphosate resistance.

The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Sambrook et al., Molecular Cloning: A Laboratory Manual, (2d Ed. 1989) (Cold Spring Harbor Laboratory, Cold Spring Harbor, N.Y.).

As used herein, a transgenic plant refers to a plant in which at least some cells are stably transformed with a heterologous DNA construct As used herein, a heterologous DNA construct refers to DNA which is artificially introduced into a cell or into a cell's ancestor. Such DNA may contain genes or DNA which would not normally be found in the cell to be transformed, or may contain genes or DNA which is contained in the cell to be transformed. In the latter case, cells are transformed so that they contain additional or multiple copies of the DNA sequence or gene of interest.

Vectors which may be used to transform plant tissue with DNA constructs of the present invention include Agrobacterium vectors, non-Agrobacterium vectors (particularly ballistic vectors), as well as other known vectors suitable for DNA-mediated transformation.

Microparticles carrying a DNA construct of the present invention, which microparticles are suitable for the ballistic transformation of a cell, are useful for transforming cells according to the present invention. The microparticle is propelled into a cell to produce a transformed cell. Where the transformed cell is a plant cell, a plant may be regenerated from the transformed cell according to techniques known in the art. Any suitable ballistic cell transformation methodology and apparatus can be used in practicing the present invention. Exemplary apparatus and procedures are disclosed in Stomp et al., U.S. Pat. No. 5,122,466; and Sanford and Wolf, U.S. Pat. No. 4,945,050 (the disclosures of all U.S. patent references cited herein are incorporated herein by reference in their entirety). When using ballistic transformation procedures, the expression cassette may be incorporated into a plasmid capable of replicating in the cell to be transformed. Examples of microparticles suitable for use in such systems include 1 to 5 μm gold spheres. The DNA construct may be deposited on the microparticle by any suitable technique, such as by precipitation. Such ballistic transformation techniques are useful for introducing foreign genes into a variety of plant species, and are particularly useful for the transformation of monocots.

Vectors that may be used to carry out the present invention include Agrobacterium vectors. Numerous Agrobacterium vectors are known. See, e.g., U.S. Pat. No. 4,536,475 to Anderson; U.S. Pat. No. 4,693,977 to Schliperoort et al.; U.S. Pat. No. 4,886,937 to Sederoff et al.; U.S. Pat. No. 5,501,967 To Offringa et al.; T. Hall et al., EPO Application No. 0122791; R. Fraley et al., *Proc. Natl. Acad. Sci. USA* 84:4803 (1983); L. Herrera-Estrella et al., *EMBO J.* 2:987 (1983); G. Helmer et al., *Bio/Technology* 2:520 (1984); N. Murai et al., *Science* 222:476 (1983). In general, such vectors comprise an agrobacteria, typically *Agrobacterium tumefaciens*, that carried at least one tumor-inducing (or "Ti") plasmid. When the agrobacteria is *Agrobacterium rhizogenes*, this plasmid is also known as the root-inducing (or "Ri") plasmid. The Ti (or Ri) plasmid contains DNA referred to as "T-DNA" that is transferred to the cells of a host plant when that plant is infected by the agrobacteria. In an Agrobacterium vector, the T-DNA is modified by genetic engineering techniques to contain the "expression cassette", or the gene or genes of interest to be expressed in the transformed plant cells, along with the associated regulatory sequences. The agrobacteria may contain multiple plasmids, as in the case of a "binary" vector system. Such Agrobacterium vectors are useful for introducing foreign genes into a variety of plant species, and are particularly useful for the transformation of dicots.

The combined use of Agrobacterium vectors and microprojectile bombardment is also known in the art (see, e.g. European Patent Nos. 486233 and 486234 to D. Bidney).

Transgenic plants may be produced using the DNA constructs of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding. Seeds may be collected from mature plants of the present invention in accordance with conventional techniques to provide seed that germinates into a plant as described herein.

Plants which may be employed in practicing the present invention include (but are not limited to) tobacco (*Nicotiana tabacum*), potato (*Solanum tuberosum*), soybean (*glycine max*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), corn (*Zea mays,* also known as maize), wheat, oats, rye, barley, rice, vegetables, ornamentals, and conifers. Vegetables include tomatoes (*Lycopersicon esculentum*), lettuce (e.g., *Lactuea sativa*), green beans (*Phaseolus vulgaris*), lima beans (*Phaseolus limensis*), peas (Pisum spp.) and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (*Tulipa* spp.), daffodils (Narcissus spp.), petunias (*Petunia hybrida*), carnation (*dianthus caryophyllus*), poinsettia (*Euphorbia pulcherima*), and chrysanthemum. Gymnosperms which may be employed to carrying out the present invention include conifers, including pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The examples which follow are set forth to illustrate the present invention, and are not to be construed as limiting thereof.

EXAMPLE 1

Plasmid Construction pRBKS and pcBBX7, kindly provided by P. Schedl (Department of Biology, Moffett Labs, Princeton, N.J.), contains the scs' and the 1.8 kb scs elements respectively.

pBHNC07, kindly provided by G. Hall, contains directly repeating 1.1 kb matrix attachment region (MAR) elements from the 3' end of the tobacco RB7 gene.

Reporter plasmid were derived from pBI221 (Jefferson et al., *EMBO J.* 6, 3901–3907 (1987)), which contains the cauliflower mosaic virus (CaMV) 35S promoter and a terminator derived from the nopaline synthase (nos) gene's polyadenylation site (Depicker et al., *J. Mol. Appl. Genet.* 1, 499–512 (1982)). In order to replace pBI221's glucuronidase (GUS) gene with a modified *Photinus pyralis* luciferase (luc*) gene (Bonin et al., *Gene* 141, 75–77 (1994)) oligo DNA linkers were used to create pBI221BglII and pBlucBglII creating BglII sites and removing the SacI and the PstI sites respectively. The 1.7 kb BglII SpeI fragment from pBlucBglII was cloned into the 3.7 kb BglII Xbal fragment of pBl221BglII to create pSluc10.

pSluc20 (containing the 35SP::luc::nosT expression cassette construct) was created by cloning the 3.0 kb luc* containing EcoRI HindIII fragment from pSluc10 into pKS (−). pSluc15 (containing the RB7MAR::35SP::luc::nosT::RB7MAR expression cassette construct) was generated by cloning that sam 3.0 kb EcoRI HindIII fragment into pGHNCO7 EcoRI HindIII. Finally, pSluc23 (containing the scs::35SP::luc::nosT::scs' construct) was created in a two step process from pSluc10, pRBKS, and pcBBX7. pSluc21 was an intermediate created by cloning pSluc10's 3.0 kb EcoRI HindIII fragment into pRBKS, and then the 1.8 kb Acc651 SalI fragment from pcBBX7 was cloned into pSluc21 Acc651 to generate pSluc23.

EXAMPLE 2

Transformation of Tobacco Cellsand Luciferase Assays

NT1, a *Nicotiana tabacum* cell line, was transformed by microparticle bombardment as described by Allen et al., *Plant Cell* 5, 603–613 (1993), using pGHNC10 (Allen et al., *Plant Cell* 8, 899–913 (1996)) as the selection plasmid. All transformants isolated 5 weeks after bombardment were grown for one week in cell suspension cultures. Cells were then scooped up with a spacula into a single well of a 96 well plate and subjected to qualitative luciferase assay as described below.

EXAMPLE 3

Qualitative Luciferase Assays

Qualitative luciferase assays were conducted by pipeting 100 μL of 0.5 mM luciferin solution over one week old calli 30 minutes prior to imaging in the Hamamatasu Agrus-50 CCD low light imaging system and viewed in pseudocolor. Comparisons were made between visibly expressing lines.

FIG. 1A shows cells transformed with a 35SP::luc::nosT expression cassette construct. Six of 19 of these control cells showed detectable expression. 35sP refers to the cauliflower mosaic virus (CaMV) 35S promoter; luc refers to a modified *Phtinus pyralis* luciferase gene; nosT refers to a terminator derived from the nopaline synthase gene polyadenylation site.

FIG. 1B shows cells transformed with an RB7MAR::35SP::luc::nosT::RB7MAR expression cassette construct. These are control transformants in which the same luciferase reporter gene was flanked by MAR sequences in a direct repeat orientation. 6 of 12 (50%) of these transformants showed detectable expression. RB7MAR refers to the tobacco RB7 gene matrix attachment region (MAR).

FIG. 1C shows cells transformed with an scs::35SP::luc::nosT::scs' construct. These transformants included 12 of 14 (86%) showing detectable expression, exhibiting a noticeable reduction in expression level variation. scs and scs' refer to the 5' and corresponding 3' scs insulators.

The foregoing examples are illustrative of the present invention, and are not to be construed as limiting thereof. The invention is defined by the following claims, with equivalents of the claims to be included therein.

That which is claimed is:

1. A method of making recombinant plant cells having increased expression of foreign DNA therein, said method comprising:

providing a plant cell capable of regeneration;

transforming said plant cell with a DNA construct comprising an expression cassette, which construct comprises, in the 5' to 3' direction, a transcription initiation region, a structural gene positioned downstream from said transcription initiation region and operatively associated therewith, and an insulator positioned: (i) 5' to the transcription initiation region, or (ii) 3' to the structural gene.

2. A method according to claim 1, wherein said transforming step is carried out by bombarding said plant cell with microparticles carrying said expression cassette.

3. A method according to claim 1, wherein said transforming step is an Agrobacterium-mediated transforming step.

4. A method according to claim 1, wherein said plant cell resides in a plant tissue capable of regeneration.

5. A method according to claim 1, further comprising the step of regenerating shoots from said transformed plant cells.

6. A method according to claim 1, further comprising the step of regenerating roots from said transformed plant cells.

7. A method according to claim 1, further comprising the step of regenerating a plant from said transformed plant cells.

8. A method according to claim 1, wherein said plant cells are monocot cells.

9. A method according to claim 1, wherein said plant cells are dicot cells.

10. A method according to claim 1, wherein said insulator is a plant insulator.

11. A method according to claim 1, wherein said insulator is an animal insulator.

12. A DNA construct comprising an expression cassette, which construct comprises, in the 5' to 3' direction, a transcription initiation region, a structural gene positioned downstream from said transcription initiation region and operatively associated therewith, and an insulator positioned: (i) 5' to the transcription initiation region, or (ii) 3' to the structural gene.

13. A DNA construct according to claim 12 carried by a plant transformation vector.

14. A DNA construct according to claim 12, wherein said insulator is a plant insulator.

15. A DNA construct according to claim 12, wherein said insulator is an animal insulator.

16. A plant cell containing a DNA construct according to claim 12.

17. A dicotyledonous plant cell containing a DNA construct according to claim 12.

18. A monocotyledonous plant cell containing a DNA construct according to claim 12.

19. A recombinant plant comprising transformed plant cells, said transformed plant cells containing a heterologous DNA construct comprising an expression cassette, which construct comprises, in the 5' to 3' direction, a transcription initiation region, a structural gene positioned downstream from said transcription initiation region and operatively associated therewith, and an insulator positioned: (i) 5' to the transcription initiation region, or (ii) 3' to the structural gene.

20. A recombinant plant according to claim 19, wherein said insulator is a plant insulator.

21. A recombinant plant according to claim 19, wherein said insulator is an animal insulator.

22. A recombinant plant according to claim 19, further comprising a termination sequence positioned downstream from said structural gene and operatively associated therewith.

23. A recombinant plant according to claim 19, which plant is a monocot.

24. A recombinant plant according to claim 19, which plant is a dicot.

25. A recombinant plant according to claim 19, which plant is a dicot selected from the group consisting of tobacco, potato, soybean, peanuts, cotton, and vegetable crops.

26. A seed that germinates into a plant according to claim 19.

27. A method according to claim 1, wherein said insulator is an scs insulator.

28. A DNA construct according to claim 12, wherein said insulator is an scs insulator.

29. A recombinant plant according to claim 19, wherein said insulator is an scs insulator.

30. A method of making recombinant plant cells according to claim 1, wherein said DNA construct further comprises a scaffold attachment region positioned 5' or 3' to said insulator.

31. A DNA construct according to claim 12 and further comprising a scaffold attachment region positioned 5' or 3' to said insulator.

32. A recombinant plant according to claim 19, wherein said DNA construct further comprises a scaffold attachment region positioned 5' or 3' to said insulator.

33. A method of making recombinant plant cells having increased expression of foreign DNA therein, said method comprising:

providing a plurality of plant cells capable of regeneration;

transforming each of said plant cells with a DNA construct comprising an expression cassette, which construct comprises, in the 5' to 3' direction, a first scs insulator, a transcription initiation region, a structural gene positioned downstream from said transcription initiation region and operatively associated therewith, and a second scs insulator;

wherein expression of the structural gene occurs in more of said plurality of plant cells compared to that which would occur in the absence of said insulator.

34. A method according to claim 33, wherein said transforming step is carried out by bombarding said plant cell with microparticles carrying said expression cassette.

35. A method according to claim 33, wherein said transforming step is an Agrobacterium-mediated transforming step.

36. A method according to claim 33, wherein said plant cells reside in a plant tissue capable of regeneration.

37. A method according to claim 33, wherein said plant cells are monocot cells.

38. A method according to claim 33, wherein said plant cells are dicot cells.

39. A method of making recombinant plant cells according to claim 33, wherein said DNA construct further comprises a scaffold attachment region positioned 5' or 3' to an insulator.

40. A method of making recombinant plant cells having increased expression of foreign DNA therein, said method comprising:

providing a plurality of plant cells capable of regeneration;

transforming each of said plant cells with a DNA construct comprising an expression cassette, which construct comprises, in the 5' to 3' direction, a first scs insulator, a transcription initiation region, a structural gene positioned downstream from said transcription initiation region and operatively associated therewith, and a second scs insulator;

said DNA construct further comprising at least one Scaffold Attachment Region (SAR), said SAR positioned 5' or 3' to an insulator, wherein expression of the structural gene occurs in more of said plurality of plant cells compared to that which would occur in the absence of said insulator.

41. A method according to claim 40, which construct comprises, in the 5' to 3' direction, a first insulator, a first Scaffold Attachment Region (SAR), a transcription initiation region, a structural gene positioned downstream from said transcription initiation region and operatively associated therewith, a second SAR, and a second insulator.

* * * * *